US00PP23137P2

(12) United States Plant Patent
Dümmen

(10) Patent No.: US PP23,137 P2
(45) Date of Patent: Oct. 23, 2012

(54) NEW GUINEA IMPATIENS PLANT NAMED 'DUEPETAUBER'

(50) Latin Name: *Impatiens hawkeri*
Varietal Denomination: Duepetauber

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 13/317,921

(22) Filed: Oct. 31, 2011

(51) Int. Cl.
*A01H 5/00* (2006.01)

(52) U.S. Cl. ..... Plt./318.6

(58) Field of Classification Search ..... Plt./318.6
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Impatiens* plant named 'Duepetauber' characterized by its upright and outwardly spreading growth habit; mounded plant habit; freely branching habit; moderately vigorous growth habit; dark green-colored leaves; freely and early flowering habit; red purple-colored flowers; and good garden performance.

1 Drawing Sheet

Botanical designation: *Impatiens hawkeri.*
Cultivar denomination: 'DUEPETAUBER'.

BACKGROUND OF THE INVENTION

The present invention relates to a new and distinct cultivar of New Guinea *Impatiens* plant, botanically known as *Impatiens hawkeri* and hereinafter referred to by the name 'Duepetauber'.

The new *Impatiens* plant is a product of a planned breeding program conducted by the Inventor in Rheinberg, Germany. The objective of the breeding program is to create new freely branching and uniform New Guinea *Impatiens* plants with large and attractive flowers.

The new *Impatiens* plant originated from a cross-pollination made by the Inventor in July, 2007 in Rheinberg, Germany of a proprietary selection of *Impatiens hawkeri* identified as code number N02-0046-001, not patented, as the female, or seed, parent with a proprietary selection of *Impatiens hawkeri* identified as code number N05-0000-003, not patented, as the male, or pollen, parent. The new *Impatiens* plant was discovered and selected by the Inventor as a single flowering plant from within the progeny of the stated cross-pollination in a controlled greenhouse environment in Rheinberg, Germany in May, 2010.

Asexual reproduction of the new *Impatiens* plant by terminal cuttings in a controlled greenhouse environment in Rheinberg, Germany since June, 2010 has shown that the unique features of this new *Impatiens* plant are stable and reproduced true to type in successive generations.

SUMMARY OF THE INVENTION

Plants of the new *Impatiens* have not been observed under all possible environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Duepetauber'.

These characteristics in combination distinguish 'Duepetauber' as a new and distinct *Impatiens* plant:

1. Upright and outwardly spreading growth habit; mounded plant habit.
2. Freely branching habit.
3. Moderately vigorous growth habit.
4. Dark green-colored leaves.
5. Freely and early flowering habit.
6. Red purple-colored flowers.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more compact than plants of the female parent selection.
2. Plants of the new *Impatiens* have smaller flowers than plants of the female parent selection.
3. Plants of the new *Impatiens* and the female parent selection differ in flower color.

Plants of the new *Impatiens* can be compared to plants of the male parent selection. Plants of the new *Impatiens* differ primarily from plants of the male parent selection in the following characteristics:

1. Plants of the new *Impatiens* flower earlier than plants of the male parent selection.
2. Plants of the new *Impatiens* and the male parent selection differ in flower color.

Plants of the new *Impatiens* can be compared to plants of New Guinea *Impatiens* 'Fisnics Purdeep', disclosed in U.S. Plant Pat. No. 17,690. In side-by-side comparisons conducted in Rheinberg, Germany, plants of the new *Impatiens* differed primarily from plants of 'Fisnics Purdeep' in the following characteristics:

1. Plants of the new *Impatiens* had shorter leaves than plants of 'Fisnics Purdeep'.
2. Plants of the new *Impatiens* had slightly smaller flowers than plants of 'Fisnics Purdeep'.

3. Plants of the new *Impatiens* and 'Fisnics Purdeep' differed in flower color as plants of 'Fisnics Purdeep' had dark purple-colored flowers.

BRIEF DESCRIPTION OF THE PHOTOGRAPH

The accompanying colored photograph illustrates the overall appearance of the new *Impatiens* plant showing the colors as true as it is reasonably possible to obtain in colored reproductions of this type. Colors in the photograph may differ slightly from the color values cited in the detailed botanical description which accurately describe the colors of the new *Impatiens* plant.

The photograph comprises a side perspective view of a typical flowering plant of 'Duepetauber' grown in a container.

DETAILED BOTANICAL DESCRIPTION

The aforementioned photograph and following observations, measurements and values describe plants grown in 10.5-cm containers during the summer in a glass-covered greenhouse in Rheinberg, Germany and under cultural practices typically used in commercial New Guinea *Impatiens* production. During the production of the plants, night temperatures averaged 18° C. and light levels averaged 4,500 lux. Plants were pinched one time about three weeks after planting and were 16 weeks old when the photograph and description were taken. In the following description, color references are made to The Royal Horticultural Society Colour Chart, 2001 Edition, except where general terms of ordinary dictionary significance are used.

Botanical classification: *Impatiens hawkeri* 'Duepetauber'.

Parentage:

*Female, or seed, parent*.—Proprietary selection of *Impatiens hawkeri* identified as code number N02-0046-001, not patented.

*Male, or pollen, parent*.—Proprietary selection of *Impatiens hawkeri* identified as code number N05-0000-003, not patented.

Propagation:

*Type*.—By terminal cuttings.

*Time to initiate roots, summer*.—About five days at temperatures of about 20° C.

*Time to initiate roots, winter*.—About seven days at temperatures of about 20° C.

*Time to produce a rooted young plant, summer*.—About three weeks at temperatures of about 20° C.

*Time to produce a rooted young plant, winter*.—About four weeks at temperatures of about 20° C.

*Root description*.—Fine, fibrous; white in color.

*Rooting habit*.—Freely branching; dense.

Plant description:

*Plant and growth habit*.—Upright to outwardly spreading growth habit; mounded plant habit; freely branching habit with about seven lateral branches; moderately vigorous growth habit.

*Plant height*.—About 14 cm.

*Plant diameter*.—About 17 cm.

Lateral branch description:

*Length*.—About 14 cm.

*Diameter*.—About 6 mm.

*Internode length*.—About 4 cm.

*Strength*.—Strong.

*Aspect*.—Initially upright to outwardly spreading.

*Texture*.—Smooth, glabrous.

*Color*.—Close to 148A.

Foliage description:

*Arrangement*.—Opposite or in whorls; simple.

*Length*.—About 8.7 cm.

*Width*.—About 3.4 cm.

*Shape*.—Ovate.

*Apex*.—Apiculate.

*Base*.—Obtuse.

*Margin*.—Serrulate with ciliation.

*Texture, upper and lower surfaces*.—Smooth, glabrous; leathery.

*Venation pattern*.—Pinnate; arcuate.

*Color*.—Developing leaves, upper surface: Close to 139A. Developing leaves, lower surface: Close to 147A. Fully expanded leaves, upper surface: Close to 139A; venation, close to 139A. Fully expanded leaves, lower surface: Close to 147B; venation, close to 147B.

*Petiole length*.—About 3.5 cm.

*Petiole diameter*.—About 3.5 mm.

*Petiole texture, upper and lower surfaces*.—Smooth, glabrous.

*Petiole color, upper and lower surfaces*.—Close to 185C.

Flower description:

*Flower type and flowering habit*.—Single rounded and flat axillary flowers; freely flowering habit, typically about seven open flowers and flower buds per lateral branch; flowers positioned above and beyond the foliar plane, flowers typically face upright or outwardly.

*Flower longevity*.—Flowers typically last about five to six days under greenhouse conditions; petals self-cleaning, gynoecium persistent.

*Fragrance*.—None detected.

*Natural flowering season*.—Year-round under greenhouse conditions; in the garden, flowering from spring until fall in Germany; early flowering habit, plants typically begin flowering about eight weeks after planting.

*Flower buds*.—Length: About 2.2 cm. Diameter: About 1.4 cm. Shape: Ovate. Color: Close to 61A.

*Flower size*.—Length: About 6 cm. Diameter: About 7.5 cm. Depth: About 3 cm.

*Petals*.—Quantity and arrangement: Five per flower in a single whorl. Length: About 3.5 cm. Width: About 4.2 cm. Shape: Obcordate. Apex: Emarginate; rounded. Base: Acute. Margin: Entire. Texture, upper and lower surfaces: Smooth, glabrous; satiny. Color: When opening and fully opened, upper surface: Close to 61A. When opening and fully opened, lower surface: Close to 61B.

*Sepals*.—Quantity and arrangement: Three in a single whorl; one modified into an elongated spur. Length: About 1 cm. Width: About 5 mm. Shape: Oval. Apex: Acute. Base: Obtuse. Margin: Entire. Texture, upper and lower surfaces: Smooth, glabrous. Color, upper and lower surfaces: Close to 147A. Spur length: About 5.8 cm. Spur diameter: At flower, about 3 mm; at apex, less than 1 mm. Spur texture: Smooth, glabrous. Spur color: Close to 59A.

*Peduncles*.—Length: About 5 cm. Diameter: About 2 mm. Angle: Upright to outward. Strength: Moderately strong; flexible. Texture: Smooth, glabrous. Color: Close to 177B.

*Reproductive organs*.—Stamens: Quantity: Five fused at anthers; filaments free. Anther length: About 7 mm. Anther shape: Oval. Anther color: Close to 11C and 60B. Pollen amount: Abundant. Pollen color: Close to 11C. Pistils: Quantity per flower: One. Pistil length: About 9 mm. Stigma shape: Crested. Stigma color: Close to 20B. Style color: Close to 11B. Ovary color: Close to 144A.

*Seeds and fruits*.—Seed and fruit production has not been observed on plants of the new *Impatiens*.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate temperatures ranging from about 5° C. to about 40° C.

It is claimed:

1. A new and distinct *Impatiens* plant named 'Duepetauber' as illustrated and described.

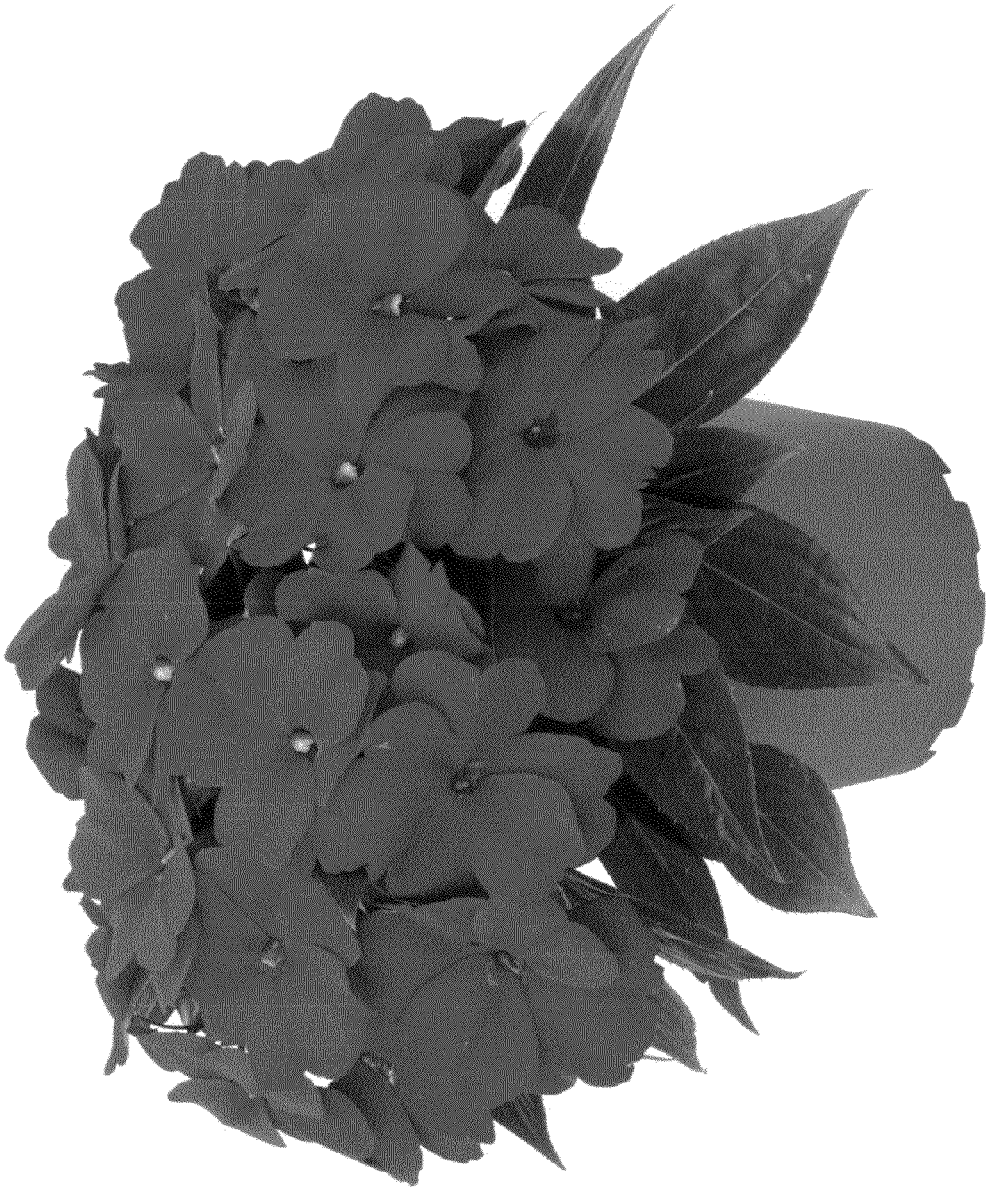

* * * * *